(12) United States Patent
Aksimentiev

(10) Patent No.: US 9,638,661 B2
(45) Date of Patent: May 2, 2017

(54) METHOD AND APPARATUS FOR CONTROLLING A FLOW OF PARTICLES BY WAY OF A THROUGH-HOLE

(71) Applicant: THE BOARD OF TRUSTEES OF THE UNIVERSITY OF ILLINOIS, Urbana, IL (US)

(72) Inventor: Aleksei Aksimentiev, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 656 days.

(21) Appl. No.: 13/773,863

(22) Filed: Feb. 22, 2013

(65) Prior Publication Data

US 2013/0220811 A1 Aug. 29, 2013

Related U.S. Application Data

(60) Provisional application No. 61/602,230, filed on Feb. 23, 2012.

(51) Int. Cl.
*G01N 27/447* (2006.01)
*G01N 33/487* (2006.01)
*G01N 15/14* (2006.01)

(52) U.S. Cl.
CPC ....... *G01N 27/447* (2013.01); *G01N 15/1404* (2013.01); *G01N 27/44791* (2013.01); *G01N 33/48721* (2013.01); *G01N 2015/1422* (2013.01); *Y10T 137/7722* (2015.04)

(58) Field of Classification Search
CPC ........... G01N 27/447; G01N 27/44791; G01N 33/48721; Y10S 977/852; Y10S 977/733; Y10S 977/72; Y10S 977/721
See application file for complete search history.

(56) References Cited

U.S. PATENT DOCUMENTS

| 2006/0073489 | A1* | 4/2006 | Li et al. ............................. 435/6 |
| 2012/0040343 | A1* | 2/2012 | Timp et al. .................. 435/6.11 |
| 2012/0258544 | A1* | 10/2012 | Chen ..................... B82Y 15/00 436/89 |
| 2013/0140649 | A1* | 6/2013 | Rogers .................... H01L 29/66 257/414 |
| 2013/0309776 | A1* | 11/2013 | Drndic et al. ................. 436/94 |

OTHER PUBLICATIONS

Aksimentiev, Aleksie, "Deciphering ionic current signatures of DNA transport through a nanopore", Nanoscale, The Royal Society of Chemistry, 2010, 468-483.

(Continued)

*Primary Examiner* — Gurpreet Kaur
(74) *Attorney, Agent, or Firm* — Guntin & Gust, PLC; Robert Gingher

(57) ABSTRACT

A system that incorporates the subject disclosure may include, for example, a method for generating an electric or pressure difference force that induces a plurality of particles to flow through a through-hole. Independently adjustable heat source in a vicinity of the through-hole induces a thermodynamic force for modifying the flow of the plurality of particles through the through-hole. Additional embodiments are disclosed.

25 Claims, 12 Drawing Sheets

(56) References Cited

OTHER PUBLICATIONS

Aksimentiev, Aleksij et al., "Microscopic Kinetics of DNA Translocation through Synthetic Nanopores", Biophysical Journal, vol. 87, Sep. 2004.
Andersen, Hans C., "Rattle: A "Velocity" Version of the Shake Algorithm for Molecular Dynamics Calculations", J. of Computational Physics, 1983, 24-34.
Baffou, Guillaume, "Femtosecond-pulsed optical heating of gold nanoparticles", Physical Review B, 2011.
Batcho, Paul et al., "Optimized particle-mesh Ewald/multiple-time step integration for molecular dynamics simulations", The J. of Chemical Physics, 2001.
Bhattacharya, Swati et al., "Molecular Dynamics Study of MspA Arginine Mutants Predicts Slow DNA Translocations and Ion Current Blockades Indicative of DNA Sequence", ACS Nano, vol. 6, No. 8, 2012, 6960-6968.
Braun, Daniel, "Creation of Entanglement by Interaction with a Common Heat Bath", vol. 89, No. 27, Dec. 30, 2002.
Comer, Jeffrey et al., "Microscopic Mechanics of Hairpin DNA Translocation through Synthetic Nanopores", Biophysical Journal, vol. 96, Jan. 2009, 593-608.
Dekker, Cees, "Solid-state nanopores", Kavli Institute of Nanoscience, 2007.
Duhr, Stefan et al., "Thermophoretic Depletion Follows Boltzmann Distribution", Physical Review Letters, 2006.
Guo, Wei et al., "Current Rectification in Temperature-Responsive Single Nanopores", Chem. Phys. Chem, 2010, 859-864.
Hanson, et al., "Electromagnetic absorption mechanisms in metal nanospheres: Bulk and surface effects in radiofrequency-terahertz heating of nanoparticles", J. of Applied Physics, 2011.
Hanson, George et al., "Optimum electromagnetic heating of nanoparticle thermal contrast agents at rf frequencies", J. of Applied Physics, 2009.
Harata, Akira et al., "Photothermal Applications of Lasers: Study of Fast and Ultrafast Photothermal Phenomena at Metal-Liquid Interfaces", Annu. Rev. Phys. Chem., 1999, 193-219.
Humphrey, William et al., "VMD: Visual Molecular Dynamics", J. of Molecular Graphics, 1996, 33-38.
Isralewitz, Barry et al., "Binding Pathway of Retinal to Bacterio-Opsin: A Prediction by Molecular Dynamics Simulations", Biophysical Journal, vol. 73, Dec. 1997.
Jerabek-Willemsen, Moran et al., "Molecular Interaction Studies Using Microscale Thermophoresis", Technology Review, 2011.
Keyser, , "Controlling molecular transport through nanopores", J. of the Royal Society Interface, 2013.
Keyser, Ulrich F. et al., "Direct forcemeasurements on DNA in a solid-state nanopore", Nature Publishing Group, 2006.
Kowalcyzk, Stefan W. et al., "Slowing down DNA Translocation through a Nanopore in Lithium Chloride", Nano Letters, 2012, 1038-1044.
Luan, et al., "Slowing and controlling the translocation of DNA in a solid-state nanopore", Nanoscale, 2012.
Mackerell, A. D. et al., "All-Atom Empirical Potential for Molecular Modeling and Dynamics Studies of Proteins", Journal Phys. Chem B, 1998, 3586-3616.
Martyna, Glenn J. et al., "Constant pressure molecular dynamics algorithms", J. of Chemical Physics, 1994.
Mast, Christof et al., "Thermal Trap for DNA Replication", Physical Review Ltrs, May 7, 2010.
Meller, Amit et al., "Voltage-Driven DNA Translocations through a Nanopore", Physical Review Letters, Apr. 9, 2001.
Mirsaidov, Utkur et al., "Slowing the translocation of double-stranded DNA using a nanopore smaller than the double helix", Nanotechnology, 2010.
Miyamoto, Shuichi et al., "SETTLE: An Analytical Version of the SHAKE and RATTLE Algorithm for Rigid Water Models", J. of Computational Chem., vol. 13, No. 8, 1992, 952-962.
Morozov, , "Thermal diffusion in disperse systems", Journal of Experimental and Theoretical Physics, vol. 88, No. 5, 1999.
Nasir, Saima et al., "Thermally controlled permeation of ionic molecules through synthetic nanopores functionalized with amine-terminated polymer brushes", Nanotechnology, 2012.
Peng, Can et al., "A novel method for fabricating sub-16 nm footprint T-gate nanoimprint molds", Nanotechnology, 2009.
Phillips, James C., "Scalable Molecular Dynamics with NAMD", Journal of Computer Chemistry, Wiley Periodicals, 2005, 1781-1802.
Roder, Paden B. et al., "Nanowire Heating by Optical Electromagnetic Irradiation", 2012, 16177-16185.
Skeel, Robert D. et al., "Correcting mesh-based force calculations to conserve both energy and momentum in molecular dynamics simulations", J. of Computational Physics, 2007.
Tjahjono, Indra K. et al., "Near-infrared light heating of a slab by embedded nanoparticles", International J. of Heat and Mass Transfer, 2008, 1505-1515.
Venkatesan, Bala et al., "DNA Sensing Using Nanocrystalline Surface-Enhanced Al2O3 Nanopore Sensors", Adv. Funct. Mater., 2010.
Viasnoff, V. et al., "Localized Joule heating produced by ion current focusing through micronsize holes", Applied Physics Letters, 2010.
Wanunu, Meni, "Electrostatic focusing of unlabelled DNA into nanoscale pores using a salt gradient", Nature Nanotechnology, 2010.
Weinert, , "Optical fluid and biomolecule transport with thermal fields", Phys. Chem. Chem. Phys., 2011, 9918-9928.
Wells, David B. et al., "Exploring transmembrane transport through α-hemolysin with grid-steered molecular dynamics", The J. of Chemical Physics, 2013.
Yameen, Basit et al., "Ionic Transport Through Single Solid-State Nanopores Controlled with Thermally Nanoactuated Macromolecular Gates", Nanotechnology, 2009, 1287-1291.
Yoo, Jejoong et al., "Improved Parametrization of Li+, Na+, K+, and Mg2+ Ions for All-Atom Molecular Dynamics Simulations of Nucleic Acid Systems", The J. of Physical Chem. Letters, 2011.

* cited by examiner

METHOD AND APPARATUS FOR CONTROLLING A FLOW OF PARTICLES BY WAY OF A THROUGH-HOLE

PRIOR APPLICATION

The present application claims the benefit of priority to U.S. Provisional Application No. 61/602,230 filed on Feb. 23, 2012, which is hereby incorporated by reference in its entirety.

STATEMENT AS TO FEDERALLY SPONSORED RESEARCH

This invention was made with government support by the Engineer Research and Development Center and the Construction Engineering Research Laboratory (ERDC-CERL), under R01-HG005115 and P41-RR005969 awarded by the National Institutes of Health (NIH), and under DMR-0955959 awarded by the National Science Foundation (NSF). The government has certain rights in this invention.

FIELD OF THE DISCLOSURE

The present disclosure relates generally to a method and apparatus for controlling a flow of particles by way of a through-hole.

BACKGROUND

It has been shown that nanopores in thin membranes can selectively transport biomolecules and other analytes and that their passage can be electronically detected.

BRIEF DESCRIPTION OF THE DRAWINGS

Reference will now be made to the accompanying drawings, which are not necessarily drawn to scale, and wherein.

DETAILED DESCRIPTION

The subject disclosure describes, among other things, illustrative embodiments of a through-hole having aspects for controlling a flow of particles therethrough. Other embodiments are included in the subject disclosure.

One embodiment of the subject disclosure entails a device including a vessel for carrying a liquid medium having a plurality of particles, a substrate having a through-hole, wherein at least a portion of the through-hole comprises one or more materials which can be selectively heated, a first conductor located above the through-hole, a second conductor located below the through-hole, wherein the first and second conductors are coupled to an electric source to cause an electric field between the first and second conductors, and wherein the electric field induces an electric force that causes a flow of the plurality of particles through the through-hole, and a source for causing the one or more materials of the through-hole to be heated, wherein the source is operable to selectively adjust heat generated in the through-hole to cause an adjustable thermodynamic force that modifies the flow of the plurality of particles through the through-hole.

Another embodiment of the subject disclosure entails a method for generating an electric force that induces a plurality of particles to flow through a through-hole, and causing the through-hole to generate heat that induces thermodynamic force for modifying the flow of the plurality of particles through the through-hole.

Yet another embodiment of the subject disclosure entails a device including a substrate having a through-hole, wherein at least a portion of the through-hole comprises one or more materials which can be selectively heated, a pressure source to generate a pressure difference that causes a flow of the plurality of particles through the through-hole, and a heat source for causing the one or more materials of the through-hole to be heated, wherein the source is operable to selectively adjust heat generated in the through-hole to cause an adjustable thermodynamic force that modifies the flow of the plurality of particles through the through-hole.

Figure 1:
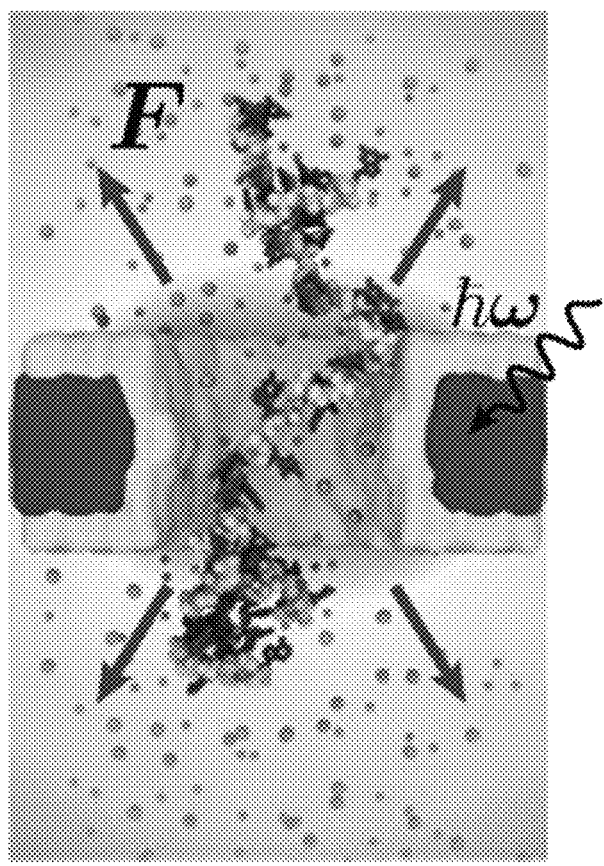
FIG. 1 depicts an illustrative embodiment of a nanopore of the subject disclosure.
Figure 2:
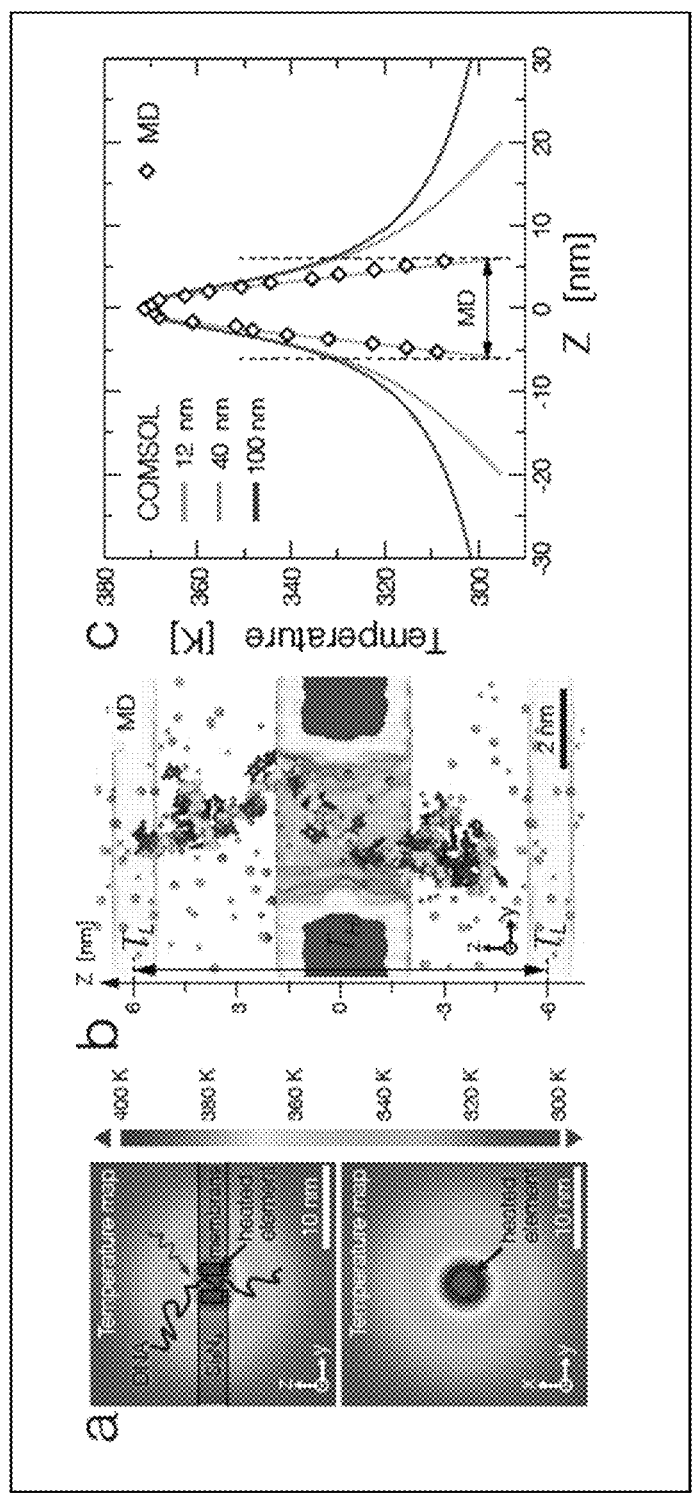
FIG. 2 depicts an illustrative embodiment of locally heated solid-state nanopores. (a) Schematics of the system considered. A thin solid-state membrane (semi-transparent gray) containing a nanopore is integrated with a heater element (dashed lines) whose temperature is regulated by means of incident radiation (red arrow). Transport and conformation of a single-stranded DNA (black) is regulated by changing the temperature of the heater element. The color maps show the steady-state temperature distribution in the system obtained as a solution of continuum heat transfer equations. (b) All-atom model of a locally heated solid-state nanopore. The Si3N4 membrane is shown in gray; the heater element in red, the backbone and bases of ssDNA are shown as yellow spheres and red sticks, respectively, $K^+$ and $Cl^-$ ions as blue and green spheres, respectively, water is not shown. Semitransparent surfaces highlight the volumes kept at 295K in the dual-bath Molecular Dynamics (MD) simulation. The black arrow indicates the extend of the simulation unit cell. (c) Temperature profiles along the nanopore axis obtained from continuum model and MD simulations. All profiles correspond to the temperature of the heater element of 400 K.

Through continuum and atomistic modeling, the subject disclosure describes the effect of local heating on the conformation and transport of single-stranded DNA through solid-state nanopores as shown in FIG. 1. In the nanopore systems considered in FIGS. 1 and 2, the temperature of the nanopore volume is controlled via a nanometer-size heater element that can be radiatively switched on and off. The local enhancement of the temperature and the sharp thermal gradients produce unwinding of single DNA strand in the nanopore. The unwinding is reversible, so that the conformation of DNA can be toggled between compact (local heating is off) and extended (local heating is off) states. Both thermal expansion and thermophoresis contribute to the reversible changes of the DNA conformation. Molecular dynamics simulations provide direct estimates of the effective thermophoretic force on single stranded DNA, which is found to be sufficiently large to alter the conformation of the DNA but not large enough to compensate the electrophoretic force of the driving transmembrane bias. The strong effect of the local heating on the electrophoretic mobility of ssDNA opens new avenues for controlling ssDNA translocation through solid-state nanopores.

Nanopores are remarkable systems that permit sensitive detection of single-molecule events by measuring ionic currents. In the case of solid-state nanopores, a common problem with carrying out such measurements is that biomolecules pass through the nanopores too quickly to accurately characterize them via ionic current measurement. Various methods have been applied to slow the translocation of biomolecules through nanopores, including optical tweezers, magnetic beads and other methods. None of the methods thus far demonstrated the desired level of control.

Temperature has been explored as a means to control translocation of DNA through nanopores. Some systems have demonstrated a considerable reduction of the DNA translocation velocity when the temperature of the system containing a biological nanopore alpha-hemolysin was lowered to 2° C. A similar principle has been applied to slow translocation of double-stranded DNA and RNA through solid-state nanopores. Temperature-responsive coating was applied to nanopores to modulate their effective diameters, which, in principle, permits regulations of the nanopore molecular transport, for example, ionic current. Experiments and continuum simulations have shown that Joule heating can create large temperature gradients in micron-size pores. Despite being discovered more than a century ago, thermophoresis, i.e. movement of molecules along a temperature gradient, has only recently been applied to control transport in micro and nano systems.

In the subject disclosure, we consider a solid-state nanopore system equipped with a local heating element surrounding the nanopore, FIG. 2a. The heater element can be a thin metallic layer introduced through a combination of atomic layer deposition and electron beam sputtering or through local modification of the structure of the membrane material. The critical requirement for the material of the element is selective absorption of electromagnetic radiation that can produce rapid local heating. Such electromagnetic heating of small nanoparticles has been demonstrated in a variety of systems. As the heater element absorbs radiation, its temperature rises and so does the temperature of the surrounding membrane and solution. However, because the size of the heater element is much smaller than the size of the membrane or solution, the steady state distribution of temperature is highly nonuniform. FIG. 2a shows the distribution of the temperature in one such system computed using the COMSOL package (see Supporting Information for details of the calculations). In both media, water and solid-state membrane, temperature drops off as $r^{-1}$, where r is the distance from the heating element. In water, however, the temperature decays faster due its lower thermal diffusivity.

To investigate the effect of such local heating on nanopore transport of DNA, an all-atom model of a locally heated nanopore system was built, FIG. 2b. In this system, a 54-nucleotide fragment of single-stranded DNA (ssDNA) is threaded halfway through a nanopore in a Si3N4 membrane, submergedin 1MKCl solution. Using established protocols of the all-atom molecular dynamics (MD) method, structural and kinetic properties of the system were investigated through a set of simulations lasting several hundreds of nanoseconds each. To model the effect of local heating, the temperature of the membrane material located more than 5 Å away from the membrane surface was controlled independently from the temperature of a 5 Å-thick slab of solution (see below detailed description of the simulation protocol). Under the periodic boundary conditions, the all-atom system is effectively infinite and, hence, heating/ cooling conditions produce a linear decay of temperature between the heated and cooled regions. Nevertheless, the temperature distributions resulting from the all-atom simulations and from continuum modeling of a much larger system, FIG. 2c, are in good agreement in the volume of interest (near the membrane), which justifies the planar heating approximation used in the all-atom simulations. Note that the average temperature inside the nanopore volume Twater is considerably lower than the temperature of the heater element TH.

Figure 3:
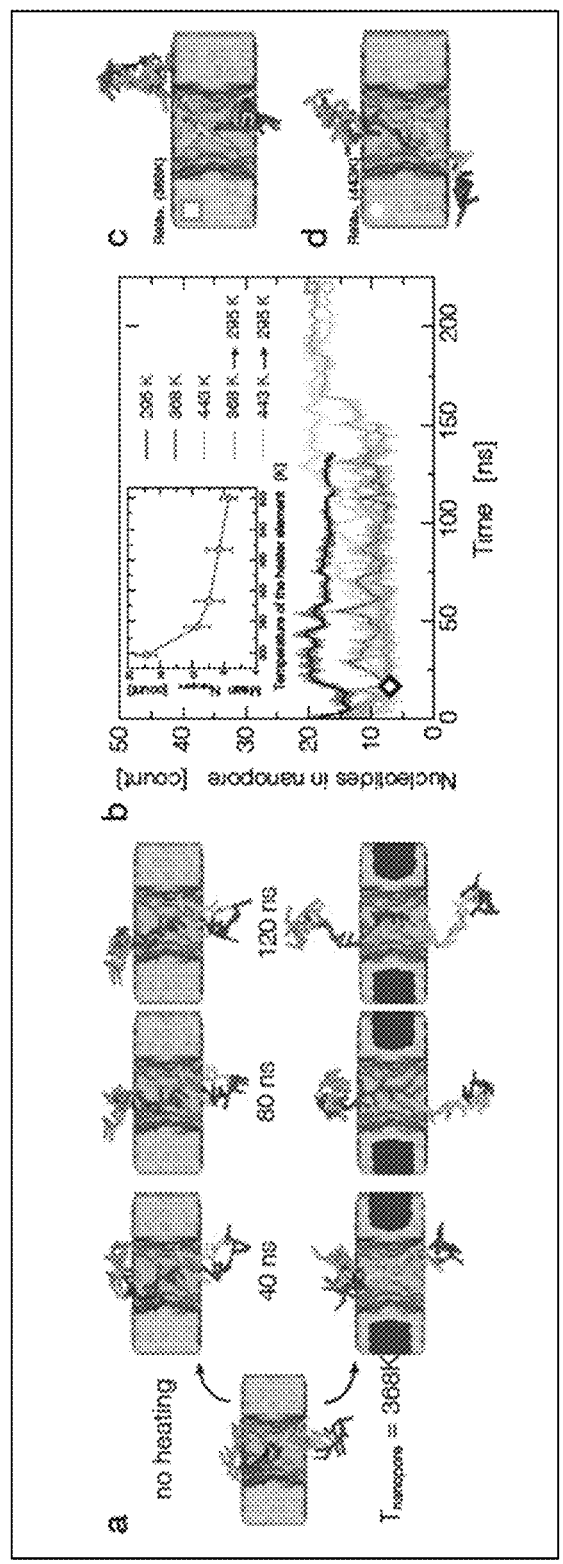
FIG. 3 depicts an illustrative embodiment for thermal unwinding of ssDNA in locally heated solid-state nanopores. (a) Snapshots illustrating typical conformations of DNA observed in MD simulations of solid-state nanopores at uniform temperature of 295 K (top row) and when the temperature of the heater element is set to 400 K. In the latter case, the temperature of the solvent in the volume of the nanopore is 368K. The DNA is shown in balls and sticks representation and colored according to its nucleotide sequences as in FIG. 1b. (b) Number of DNA nucleotides in the nanopore volume during MD simulations performed at several values of the heater element's temperature. Black, red and blue traces began from the same conformation (shown in panel a) and corresponds to the nanopore volume temperature of 295, 368 and 443 K, respectively (TH=295, 400 and 500 K). The yellow and green traces illustrate conformational relaxation of ssDNA after the local heating of 400 and 500K was turned off. The starting points of the relaxation simulations are marked by the 'diamond' symbol. The inset shows the average number of nucleotides in the nanopore volume as a function of the heater temperature. (c, d) Conformations of DNA at the end of the 200 ns relaxation simulations (yellow and green traces in panel b)

The presence of a temperature gradient was found to produce a considerable change in the conformation of the DNA fragment, FIG. 3a. Thus, in the system having uniform room temperature, the DNA fragment maintained its compact structure both inside and outside the nanopore. However, upon assigning a heater element a temperature of 400 K, the fragment of DNA confined in the nanopore visibly straightened. To quantify the change in the conformation of DNA caused by local heating, the number of nucleotides present in the nanopore volume Npore was plotted versus time for a set of simulations carried out at several temperatures of the heater element, FIG. 3b. In all simulations, DNA reached an unwound state characterized by a low value of Npore in less than 20 ns. The average number of DNA nucleotides confined in the nanopore was found to decrease as the temperature of the heater element increased, FIG. 3b.

To determine if such a conformational change is reversible, the temperature control of the heater element was switch off after DNA unwinding was observed in the TH=400 and 500K simulations, FIG. 3b. In experiment, switching off of the heater element can be realized by turning off the source of radiating heating. In simulations, the temperature of the system was observed to reach a uniform 295K value within 5 ns. Such rapid cooling is possible because of the nanometer dimensions of the heater element. [31] In both simulations, DNA was observed to relax back to the conformations typical of room temperature simulations, FIG. 3d, and FIG. 3c. The 200 ns time scale of con-formational relaxation, FIG. 3b, is considerably longer than the unwinding times scale of 20 ns and the thermalization time scale of 5 ns.

Figure 6:
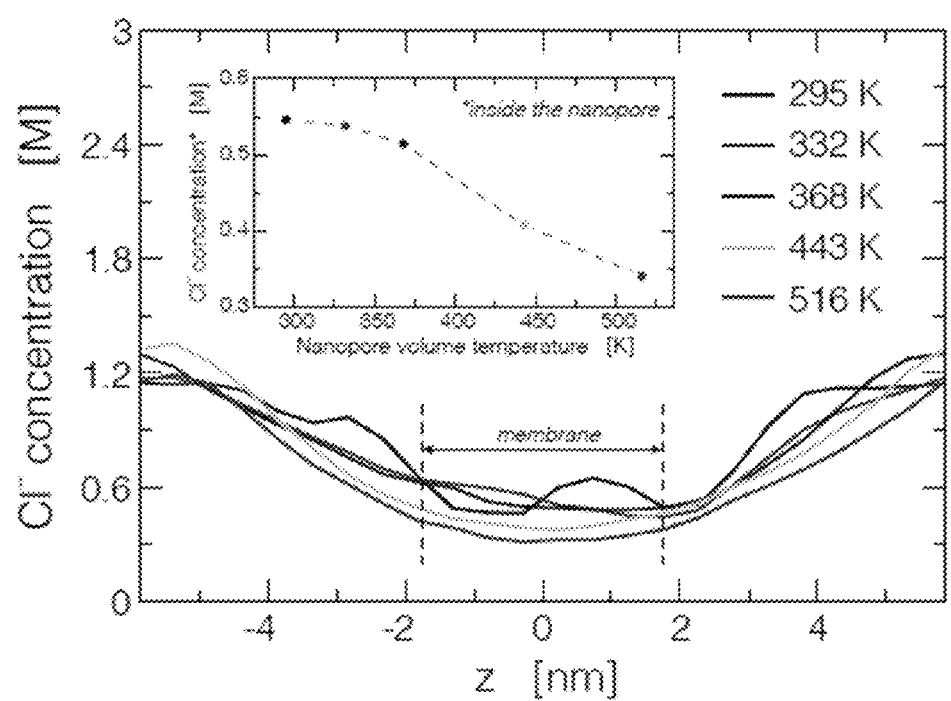
FIG. 6 depicts an illustrative embodiment of an ion concentration in locally heated nanopore systems. The local molar concentration of $Cl^-$ ions is plotted along the axis of the nanopore for several values of the nanopore temperature. Vertical dashed lines indicate the location of the Si3N4 membrane. Inset Average value of $Cl^-$ concentration within the nanopore volume as a function of the volume's average temperature.

The unwinding of ssDNA in locally heated nanopores can result from the elevated temperature of the nanopore volume, the thermophoretic force pulling the two ends of DNA in opposite directions, and increased electrostatic self-repulsion caused by a change of the electrolyte condition in the nanopore. A plot of $Cl^-$ concentration along the nanopore axis for several values of the nanopore volume temperature, FIG. 6, revealed only a moderate decrease of ion concentration, which was assessed as insufficient to produce the observed changes in the DNA conformation.

The effect of temperature on the conformation of a DNA strand was elucidated in the absence of thermophoresis by performing the simulations of the ssDNA strand in a uniformly heated 1 M KCl solution. FIG. 7a illustrates a typical simulation system. As in our simulations of the locally heated nanopore systems, ssDNA was observed to change its conformation in bulk solution with temperature: the radius of gyration of ssDNA increased, FIG. 7b. To quantitatively compare the conformations of DNA in the simulations of the nanopore and bulk solution systems, the number of DNA nucleotides located within 17.5 Å were counted from the DNA's center of mass in bulk solution simulations and within 17.5 Å from the nanopore's center in the nanopore simulations. Computed thereby numbers of nucleotides were found to be in general agreement with one another, FIG. 7c, indicating the dominant role of the elevated temperature in the observed unwinding of ssDNA in the locally heated nanopore systems. The results are not entirely surprising, as the temperature variation is small inside the nanopore volume, FIG. 2c. At low to moderate temperatures, however, the number of nucleotides in the nanopore system was typically smaller than that in the corresponding bulk solution system, which indicates the effect of steric confinement that prevents complete unwinding of DNA.

To evaluate the effect of the thermophoretic force, the DNA strand was cut in halve and moved, as a rigid body, along the pore axis such that one end of its halves juxtaposed with the center of the nanopore. That end of the DNA strand was harmonically restrained to the center of the nanopore, expecting that the effective force of the thermal gradient would displace the DNA strand away from the attachment point, revealing the magnitude of the effective force as the product of the average displacement and the spring constant of the restraining potential. Unfortunately, significant fluctuations of the force due to interaction of the DNA with the nanopore surface did not allow one to draw any quantitative conclusions about the magnitude of the thermophoretic force within the time scale of our simulations.

Figure 4:
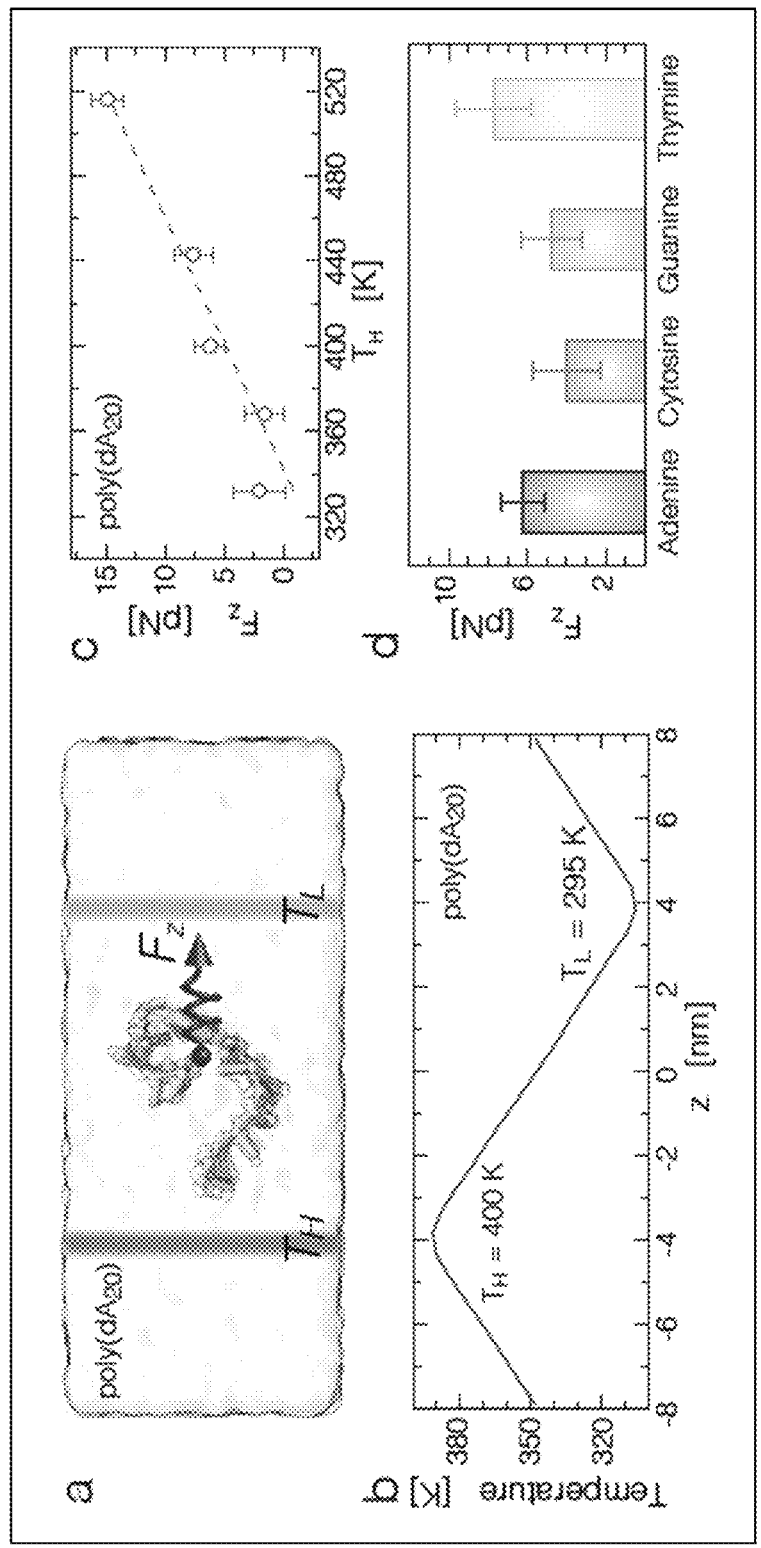
FIG. 4 depicts an illustrative embodiment of MD simulations of the effective thermophoretic force. (a) Setup of the simulations. A 20-nucleotide DNA homopolymer (poly(dA)$_{20}$ is shown) is placed between two temperature-controlled regions depicted as red and blue stripes. The center of mass of the homopolymer is harmonically restrained to the point equidistant from the highlighted regions. The average displacement of the DNA fragment indicates the effective force of the temperature gradient. (b)Temperature profile along the z-axis in the simulations of the effective thermophoretic force. (c) Simulated thermophoretic force versus temperature of the hot region TH; TL=295 K in all simulations. (d) Average thermophoretic force for the four DNA homopolymersat TH=400 K and TL=295 K.

The magnitude of the thermophoretic force was measured using a simulation system shown in FIG. 4a. Displacement of a 20-nucleotide homopolymer restrained via a harmonic potential to a point equidistant to the regions of high and low temperature revealed the magnitude and direction of the thermophoretic force. FIG. 4b illustrates a typical profile of temperature attained in these simulations. For the four DNA homopolymer sequences tested, the thermophoretic force was found to push the DNA strand from the region of high temperature toward the region of low temperature. The magnitude of the force was found to linearly scale with the temperature gradient, FIG. 4c. The magnitude of the thermophoretic force experienced by a 20-nucleotide fragment at a 100K difference over 8 nm was approximately 6 pN, 0.3 pN per nucleotide. Within the statistic error of our computational experiments, all four DNA homopolymers experienced approximately the same thermophoretic force at the same temperature gradient. The results of these simulations suggest that the thermophoretic force can have a considerable effect on the conformation of DNA fragments located in the immediate vicinity of the heater element outside the nanopore, producing pronounced stretching. Thus, a DNA fragment of 1,000 nucleotides placed halfway through the temperature-controlled nanopore would experience a stretching force of at least 3 pN due to thermophoresis when the temperature of the heater is 400 K.

Figure 5:
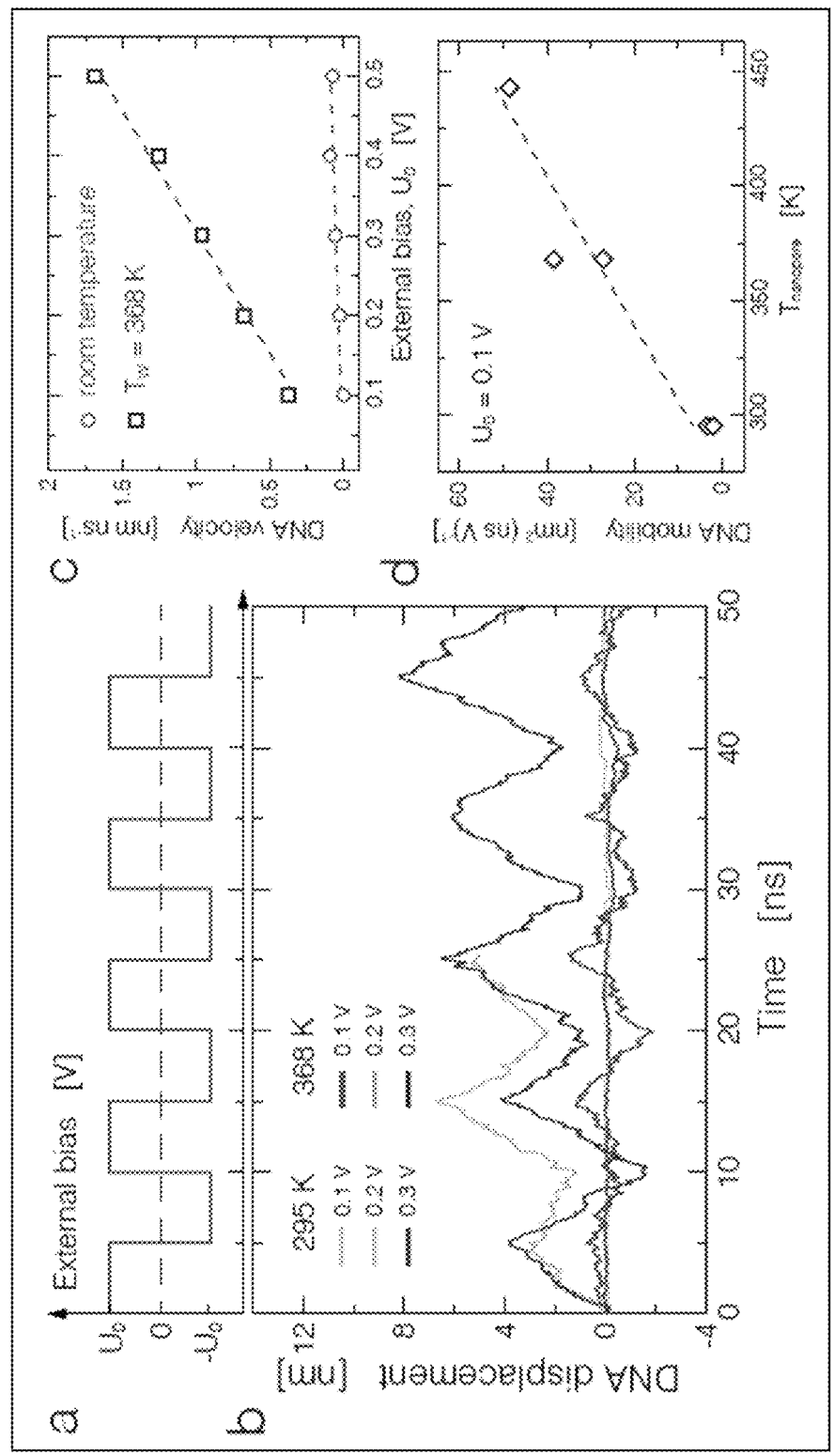
FIG. 5 depicts an illustrative embodiment of electrophoretic motion of DNA through a nanopore assisted by local heating. (a) Profile of the alternating transmembrane bias applied in the simulations described in panel b. (b) DNA translocation driven by alternating electric field. Shown is displacement of ssDNA through the nanopore in MD simulations performed at uniform room temperature and when the temperature of the heater element is set to 400K (the temperature of the nanopore volume TW=368 K). (c) Translocation velocity of ssDNA as a function of the transmembeane bias extracted from the simulations of the two nanopore systems under alternating electric field. Lines show linear fits to the data producing the following estimates of the electrophoretic mobility: $\mu 295K=2.0$ nm/(ns·V), and $\mu 368K=38.5$ nm$^2$/(ns·V). (d) Electrophoretic mobility of ssDNA versus temperature of the nanopore volume, TW. Dashed line indicates a linear fit to the data; the slope is 0.003 nm$^2$/(ns·V·K)

To determine the effect of local heating on the process of electrophoretically-driven DNA translocation, we simulated our locally heated nanopore systems under several transmembrane bias conditions. In a set of computational experiments, our solid-state nanopore systems were subject to a transmembrane electric potential that switched direction every 5 ns, FIG. 5a. In the simulations performed at room temperature, displacement of the ssDNA molecule during each 5 ns half-cycle did not exceed 0.1 nm for the transmembrane biases in the 100 to 300 mV range, FIG. 5b. Setting the temperature of the heater element to 400 K considerably increased the amplitude of ssDNA displacement through the nanopore, FIG. 5b. The average velocity of DNA translocation extracted from the trajectories obtained under the alternating field conditions are shown in FIG. 5c. By utilizing local heating, the electrophoretic mobility of ssDNA could be increased by a factor of 20.

Thus, the results suggest the possibility of controlling the electrophoretic transport of ssDNA through a solid-state nanopore by radiatively switching on and off the local heating element surrounding the nanopore. To determine conditions for exercising such a control, we first investigated the electrophoretic mobility of ssDNA during the on/off cycle of the heater element. For our "off" state, we chose the following three DNA conformations: the initial room-temperature conformation shown in FIG. 3a, and the two conformations attained by the DNA strand at the end of the relaxation trajectories, FIG. 3c and FIG. 3d. As representative conformations for the "on" state, we chose steady-state conformations from two independent trajectories at TH=400 and 500 K. Each system was simulated under a 100 mV transmembrane bias and the pertinent temperature of the heater element (295, 400 or 500 K) for 20 or 40 ns. The resulting electrophoretic mobility of DNA as a function of the heater temperature is shown in FIG. 5d. Consistent with the results of the alternating electric field simulations, DNA mobility was found to strongly depend on the temperature of the heater element.

In another set of simulations, we attempted to control DNA transport by switching the local heating on and off while maintaining a constant transmembrane bias. We found the force driving the relaxation of ssDNA from unwound (high mobility) to compact (low mobility) conformations to be considerably smaller than the electrophoretic force driving DNA translocation, which prevented ssDNA from reaching the compact state and thereby attaining a lower electrophoretic mobility. Thus, to use local heating as a means of controlling DNA transport, switching off of the local temperature must occur at the same time or after switching off of the transmembrane bias. Upon relaxation of the DNA conformation to a compact state, the transmembrane bias can be switched back on to transport DNA at a reduced rate.

The subject disclosure discusses the behavior of a single-stranded DNA molecules in solid-state nanopores equipped with a local heating element. It was found, that local heating augments DNA unsticking from the nanopore surface and promotes unwinding of the DNA fragment threaded through the nanopore. The thermophoretic forces was found to be too weak to counter the electrophoretic force of the transmembrane bias but large enough to alter the conformation of a DNA molecule beyond the nanopore. The results indicate that local heating can be employed to regulate the velocity of ssDNA transport through solid-state nanopores. Possible practical applications of the locally-heated solid-state nanopores range from detection of DNA binding proteins to DNA sequencing to drug design.

Simulation Methods

Continuum Model.

A continuum model of a heated solid-state nanopore system was built using the COMSOL software package. A cylindrical pore of 3.5 nm diameter was made in a 3.5 nm-thick membrane. The properties of the membrane material were set to match the properties of silicon nitride: heat capacity $c_p^m$=710 J(kg·K)$^{-1}$, density $\rho^m$=3310 kg·m$^{-3}$, and thermal conductivity $k^m$=2 W·(m·K)$^{-1}$. The membrane was surrounded by water, $c_p^w$=4181.3 J(kg·K)$^{-1}$, $\rho^w$=1000 kg·m$^{-3}$, and $k^2$=0.58 W·(m·K)$^{-1}$. The entire simulation domain was a cube 12, 40, or 100 nm on a side. The heating element was modeled as a cylindrical ring concentric with the nanopore. The inner surface of the ring had the same diameter as the nanopore, the outer diameter was 4.5 nm. The height of the heating element was 1 nm; the heating element was located in the middle of the membrane. The temperature of the heating element was set to TH; the Dirichlet boundary *To whom correspondence should be addressed conditions(T=295K) applied at all sides of the simulations domain. After building the standard mesh, the system of coupled heat transfer equations for fluid and solid was solved in the COMSOL 4.3 software package (Heat Transfer module) to find a steady-state solution using GMRES solver and damped Newton's method.

General MD Methods.

All molecular dynamics simulations were performed using the program NAMD2, periodic boundary conditions, the CHARMM27 parameter set for water, ions and nucleic acids, CHARMM-compatible parameters for silicon nitride, and ion-pair specific corrections to the Lennard-Jones parameter 6. All simulations employed a 2-2-6-fs multiple time stepping, SETTLE algorithm to keep water molecules rigid, RATTLE algorithm to keep rigid all other covalent bonds involving hydrogen atoms, a 7-8 Å cut off for van der Waals and short-range electrostatic forces. Long-range electrostatic interactions were computed using the particle mesh Ewald (PME) method[7] over a 1.0 Å-spaced grid with the net momentum removed before every full electrostatics calculation (zero Momentum feature of NAMD2).[8]

All-Atom Model of Single-Stranded DNA.

For our MD simulations of the Si3N4 nanopore system, we prepared an all-atom model of single-stranded DNA of the following nucleotide sequence: 5'-AAAAAAAAAC-CCCCCCCCCCCCCTTTTTTTTTTTTTGGGGGGG-GGGGGGGG-3'. The initial conformation of the DNA was taken from our previous simulation of the full-length MspA-DNA system. The same DNA fragment was used in our simulations of DNA in bulk solutions. For our simulations of the thermophoretic force in solid-state nanopores, the DNA strand was cut in half, see 'Thermophoretic force measurements' paragraph below. For our simulations of the average thermophoretic force in bulk solution, four DNA homopolymers containing twenty DNA nucleotides each were prepared using DNA conformations extracted from our previous simulations.

All-Atom Model of the Solid-State Nanopore-DNA System.

An all-atom model of a 3.5 nm thick $Si_3N_4$ membrane was built according to procedures described elsewhere. A double-cone pore of a 3.5 nm diameter in its center and 4.3 nm-diameter openings at both sides was cut by removing atoms from the membrane. A 54-nucleotide DNA strand was added such that it threaded half-way through the nanopore. The system was then solvated using the Solvate plugin of VMD. Following that, the system was neutralized by adding $K^+$ and $Cl^-$ ions in the amounts necessary to produce a 1M solution. The final system was a 117 Å-long hexagonal prism with a side of 79 Å; hexagonal periodic boundary conditions were applied in the xy-plane. In all simulations of the $Si_3N_4$ systems, atoms of the membrane were harmonically restrained to their initial coordinates. The spring constant of the harmonic constraints applied to the surface or bulk atoms of the membrane was 10 or 1 kcal/(mol·Å$^2$), respectively. To reduce adhesion of DNA to the nanopore surface, a custom potential was applied to DNA atoms by means of the GridForce feature of NAMD2.

Upon building, each system underwent 4,000 steps of energy minimization using the conjugate gradient method. Following that, each system was equilibrated for 6 ns in the NPT ensemble, i.e. constant number of particles N, pressure P and temperature T. During this equilibration, a Langevin thermostat with a damping coefficient of 0.02 ps$^{-1}$ kept the temperature at 295 K; Nosé-Hoover Langevin piston pressure control was used to maintain the pressure of 1 atm by adjusting the system dimension normal to the plane of the Si3N4 membrane. The mean length of the system during the last 4 ns of the NPT equilibration was used in all production simulations.

In our simulations of electric field-driven transport of DNA through the nanopores, an external electric field was applied in the direction normal to the membrane (along the z axis). The external fields are reported in terms of a transmembrane voltage difference V=−ELz, where E is the electric field strength and Lz is the length of the simulation system in the z direction.

Single-Stranded DNA in a Uniformly Heated Bulk Solutions.

The single-stranded DNA molecule used in our nanopore simulations was also simulated in a uniformly heated solution. To prepare the simulation system, the 54-nucleotide DNA strand was solvated in a volume of pre-equilibrated water molecules. $K^+$ and $Cl^-$ ions were added to produce a neutral 1M solution. The system was then equilibrated in the NPT ensemble for 6 ns; the mean dimensions of the system during the last 4 ns of equilibration were used in the production NVT simulations. Equilibration steps were repeated for the following temperatures: 295 K, 350 K, 400 K, and 500 K. Compared to the 295K system, the total volume of the 350K, 400K, and 500K systems increased by 5.2, 11.3 and 32.9%, respectively. The resulting dimensions of the final simulation system were sufficient to avoid DNA interactions with its periodic cell images, see FIG. 6b.

Dual Thermal Bath Simulations of all-Atom Systems.

Two thermal baths were used to produce a stationary temperature gradient in our all-atom systems. In the case of Si3N4 nanopore systems, the temperature gradient was established between the heated membrane and a slab of cooled water. The temperature of the membrane was controlled by the Langevin thermostat applied to the membrane atoms located 5 Å away from the nanopore surface. At the same time, the Lowe-Andersen thermostat was applied to water molecules confined inside a 5 Å-wideslab. The slab was arranged parallel to the membrane and positioned such that two equal-magnitude opposite-direction temperature gradients were formed on the sides of the membrane under the periodic boundary condition, FIG. 1c of the main text. Importantly, our custom implementation of the Lowe-Andersen thermostats allowed us to control temperature of a certain volume inside our simulation system. Water, ions and DNA could freely enter and exit the volume subject to the Lowe-Andersen thermostat, whereas the Langevin thermostat applied to a fixed set of membrane atoms.

In our simulations of the effective thermophoretic force in bulk solution, two Lowe-Andersen thermostats were employed, both of which were confined to a 5 Å-wide slabs arranged parallel to each other. The location of the slabs was chosen such that two equal-magnitude opposite-direction temperature gradients were produced between the slabs under the periodic boundary conditions.

The dual temperature bath simulations were performed with a custom version of NAMD2. The GridForce feature of NAMD2 was used to define regions in the system where individual Lowe-Andersen thermostat were applied to select sets of atoms.

Direct Measurements of the Thermophoretic Force.

The effective force of a temperature gradient on a DNA fragment was measured using four simulation systems each containing a 20 nucleotide fragment of ssDNA (poly(dA)20, poly(dC)20, poly(dG)20 or poly(dT)20) submerged in 1MKCl solution approximately 60×60×160 Å$^3$ in volume. Following energy minimization, each system was equilibrated for 6 ns in the NPT ensemble to obtain the average dimensions of the system. The DNA molecule was initially placed equidistant from the two different-temperature thermostated regions, which were 5 Å-wide rectangular slabs, FIG. 3a. Room temperature of 295K was maintained in one of the slab regions, whereas the temperature of the other region was set to a higher value (TH), producing a stationary temperature gradient between the slabs. Steered molecular dynamics (SMD) protocol was used to restraint the center of mass of the DNA fragment. The motion of the DNA fragment was restrained only in the direction normal to the thermostat regions (along the z axis); the DNA could freely move parallel to the slabs. The SMD spring constant of kz=0.29 kcal/(mol·Å$^2$) was used, which corresponds to the force of ~20 pN for a displacement of dz=1 Å. During the course of a constant volume simulation, displacement of the center of mass of the DNA fragment was recorded every 9.6 ps and used to determine the effective force experiences by the fragment as Feff(t)=kz·dz(t). The average force was determined by averaging the instantaneous force values over the entire trajectory. The poly(dA)20 system was simulated at several temperature gradients corresponding to TH=350 K, 400 K, 500 K. All other homopolymers were simulated only for one temperature gradient corresponding to TH=400 K. Systems containing poly(dC)20, poly(dG)20 and poly(dT)20 fragments were simulated for 80 ns, whereas simulations of the poly(dA)20 system lasted ~170 ns each.

Analysis of the MD Trajectories

Number of Nucleotides.

To determine the number of DNA nucleotides confined in a nanopore, the number of atoms inside the nanopore was determined for each nucleotide and then divided by the total number of atoms in that nucleotide. Atoms were considered to reside inside the nanopore if their coordinates satisfied the condition: −17.5<z<17.5 Å, where z=17.5 Å and z=−17.5 Å define the top and bottom surfaces of the membrane, correspondingly. Obtained fractions across all nucleotides were then added up to yield the aggregate number of nucleotides in the nanopore, Npore.

To quantitatively compare conformations of DNA in the heated nanopore and free solution simulations, for both types of the simulations we computed the number of nucleotides confined in a spherical volume of a 17.3 Å radius, Nsp. In the case of the heated nanopore simulations, the volume's center was in the middle of the nanopore. In the case of the free solution simulations, the volume's center was at the center of mass of the DNA fragment. Comparison between Npore to Nsp is shown in FIG. 6c.

DNA mobility and translocation velocity. To compute the velocity of DNA translocation through a nanopore, velocity of each nucleotide in the nanopore was computed as displacement of its center of mass divided by the time during which this displacement occurred. Instantaneous velocity of DNA translocation vDNA(t) through the solid-state nanopore was taken as the average velocity of all nucleotides confined inside the nanopore, i.e. nucleotides whose centers of mass satisfied the condition −17.5<z<17.5 Å. Reported in FIG. 4, DNA displacement was then computed as:

$$L(t) = \int_0^t v_{DNA}(\tau) d\tau. \quad (1)$$

The average velocity of DNA translocation was extracted from a linear fit to the plot of the DNA displacement. Electrophoretic mobility of DNA was then readily calculated as the translocation velocity divided by the applied electric field. In our analysis of the simulations employing an alternating electric field, we first combined traces corresponding to the same direction of the applied field into one and then proceeded as described above.

Temperature Distribution in all-Atom Systems.

To compute the distribution of temperature in our all-atom systems, velocities of all atoms in the system were recorded every 9.6 ps along with their coordinates. Instantaneous temperature in a particular subvolume was computed as: $T = 2K/(NDOF\, k_B)$, where K is the total kinetic energy of all atoms in that volume, NDOF is the number of degrees of freedom of all atoms in that volume and kB is the Boltzmann constant. Although stable temperature gradients established in our systems in ~1 ns, we typically performed averaging over 10 ns intervals. In our analysis of the thermophoretic force simulations (FIG. 3), the temperature was calculated using 5 Å-wide layers arranged perpendicular to the z axis. Analysis of the solid-state nanopore systems was performed using cubic bins with a side of ~5 Å. To plot the temperature profile through the nanopore (FIG. 1c), data from the bins that the nanopore axis passes through were used.

Ion Concentration Profile.

Figure 7:
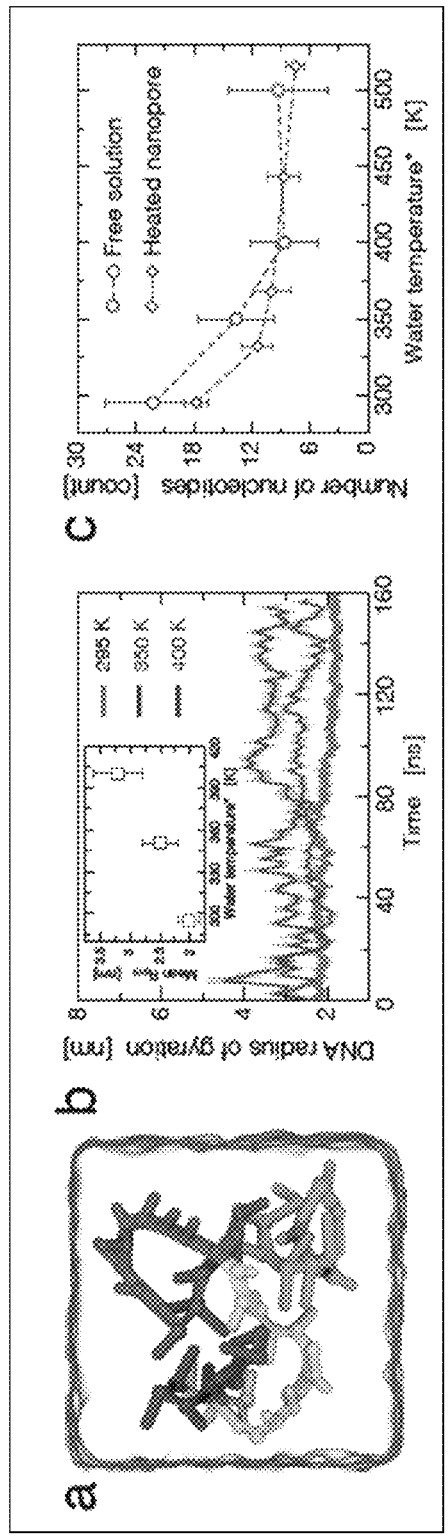
FIG. 7 depicts an illustrative embodiment of MD simulations of single-stranded DNA in bulk solutions of different uniform temperatures. (a) Representative conformation of a DNA strand in a simulation performed at T=332K. The DNA strand is colored according to its nucleotide sequence (blue adenine, yellow cytosine, red thymine and green guanine); the solvent is shown as a semitransparent surface. (b) Radius of gyration of the DNA strand in MD simulations of several bulk solution systems. (c) Average number of DNA nucleotides within 1.75 nm from the center of mass of the DNA strand in bulk solution simulations as a function of the solution temperature. For comparison, the number of nucleotides within 1.75 nm from the geometrical center of the Si3N4 nanopores (heated nanopore simulations) is plotted versus the average temperature of the solution inside the nanopore.
Figure 8:
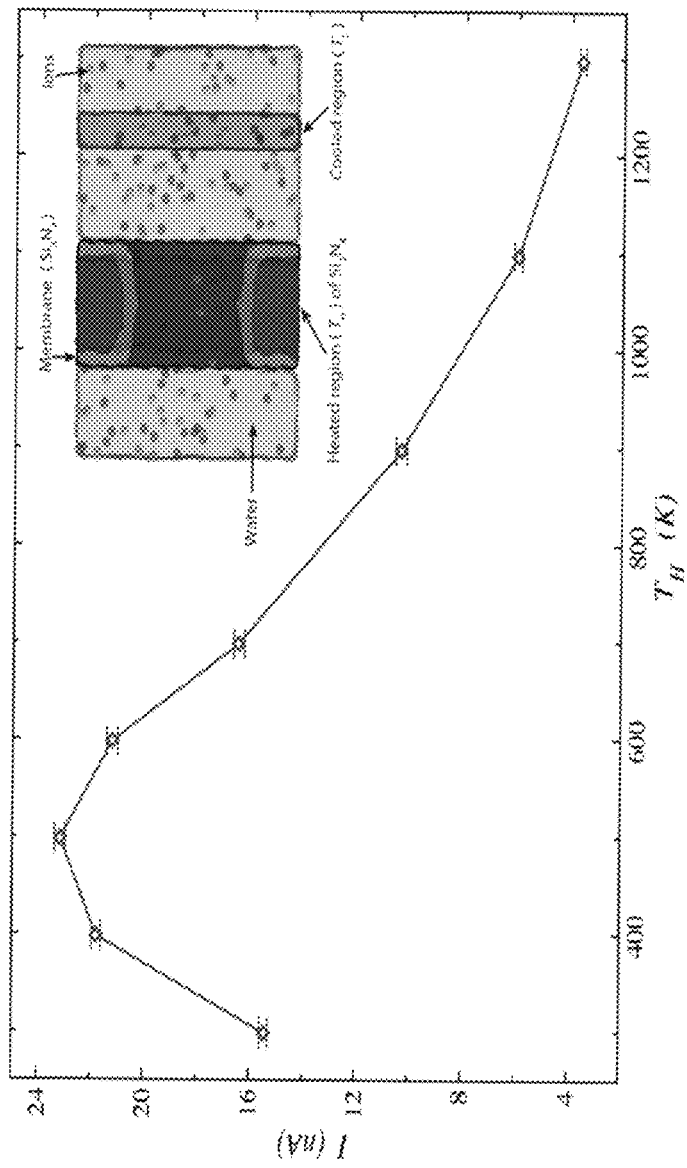
FIG. 8 depicts an illustrative embodiment of a dependence of an ionic current through a solid-state (Si3N4) nanopore on the temperature of the heated region of the nanopore obtained from all-atom MD simulations. Simulations were performed using periodic boundary conditions for 1M KCl solution and the applied bias of 1 V. Heated region of the solid-state nanopore was defined as 5 Å away from the water. A region away from the nanopore was defined where the temperature of the water was kept at 298K. The data demonstrates regulating ionic current by locally heating the membrane that contains a nanopore.
Figure 9:
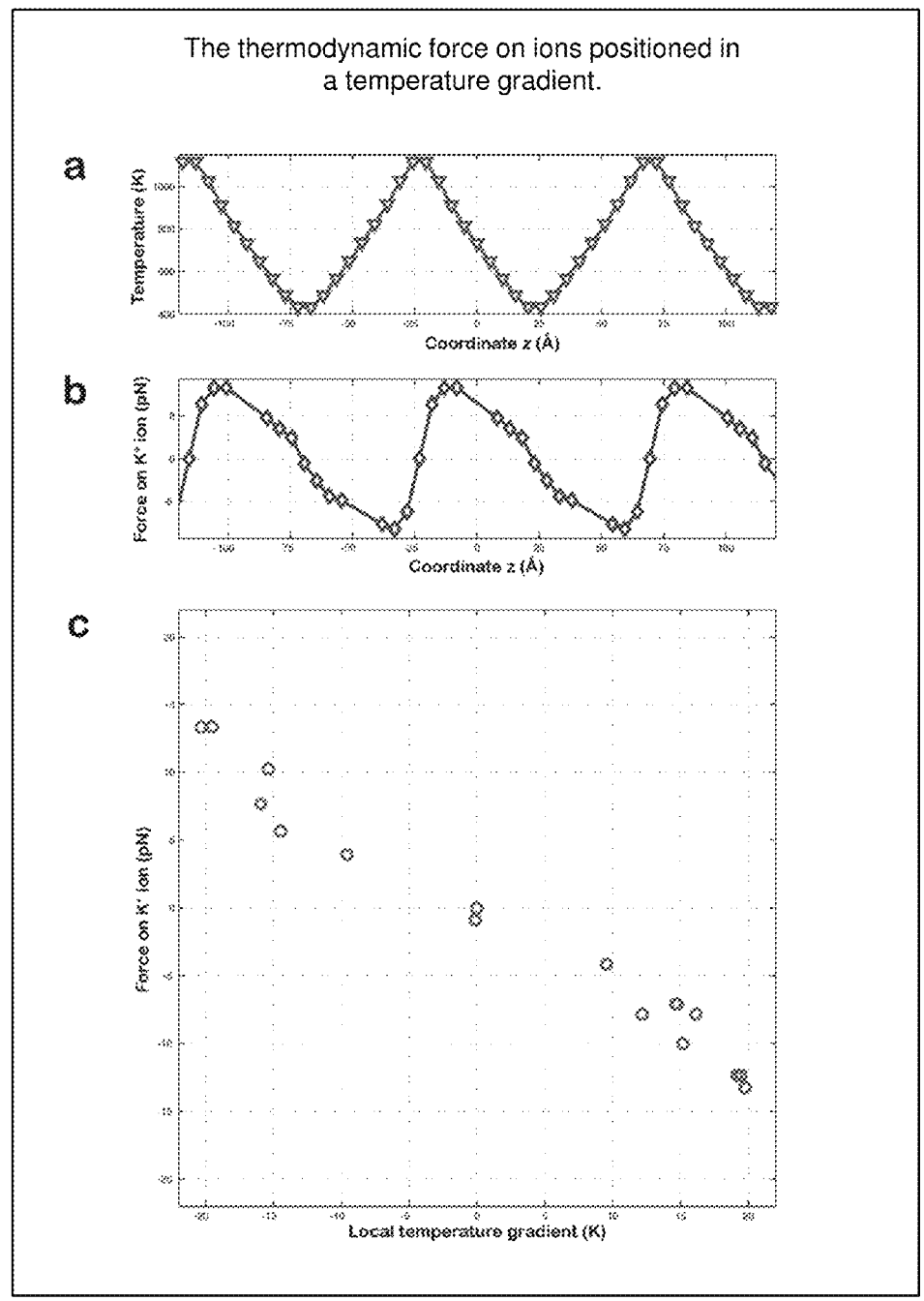
FIG. 9 depicts an illustrative embodiment of all-atom MD simulations of the effectic thermodynamic force on a single ion in 1M KCl solution. (a) Temperature versus coordinate z. (b) Force experienced by the K ion versus coordinate z. (c) Dependence of the force experienced by the K ion on the local temperature gradient. The data illustrate the possibility of applying a thermodynamic force to an ion due to temperature gradient, which can be used to control transport of biomolecules through a nanopore.

FIG. 7 shows the profile of Cl⁻ molar concentration in our solid-state nanopore systems. To compute the concentration profiles, the system was split into ~5 Å thick 12 Å-radius cylindrical slabs along the z axis. The number of ions within in each slab was averaged over the corresponding MD trajectory and divided by the volume of the slab. The radius of the cylindrical slabs was chosen to minimize the effect of specific ion-nanopore surface interactions while providing statistically significant number of ion observations.

It has been shown that nanopores in thin membranes can selectively transport biomolecules and other analytes and that their passage can be electronically detected. The subject disclosure describes a method to enhance the selectivity of nanopore analyte transport and the sensitivity of nanopore analyte detection. An illustrative embodiment of the subject disclosure shown in FIGS. 8-11 includes creating a temperature gradient between the nanopore membrane and the environment, which imparts a thermodynamic force on the analyte, altering its behavior in the vicinity of the nanopore.

Figure 10:
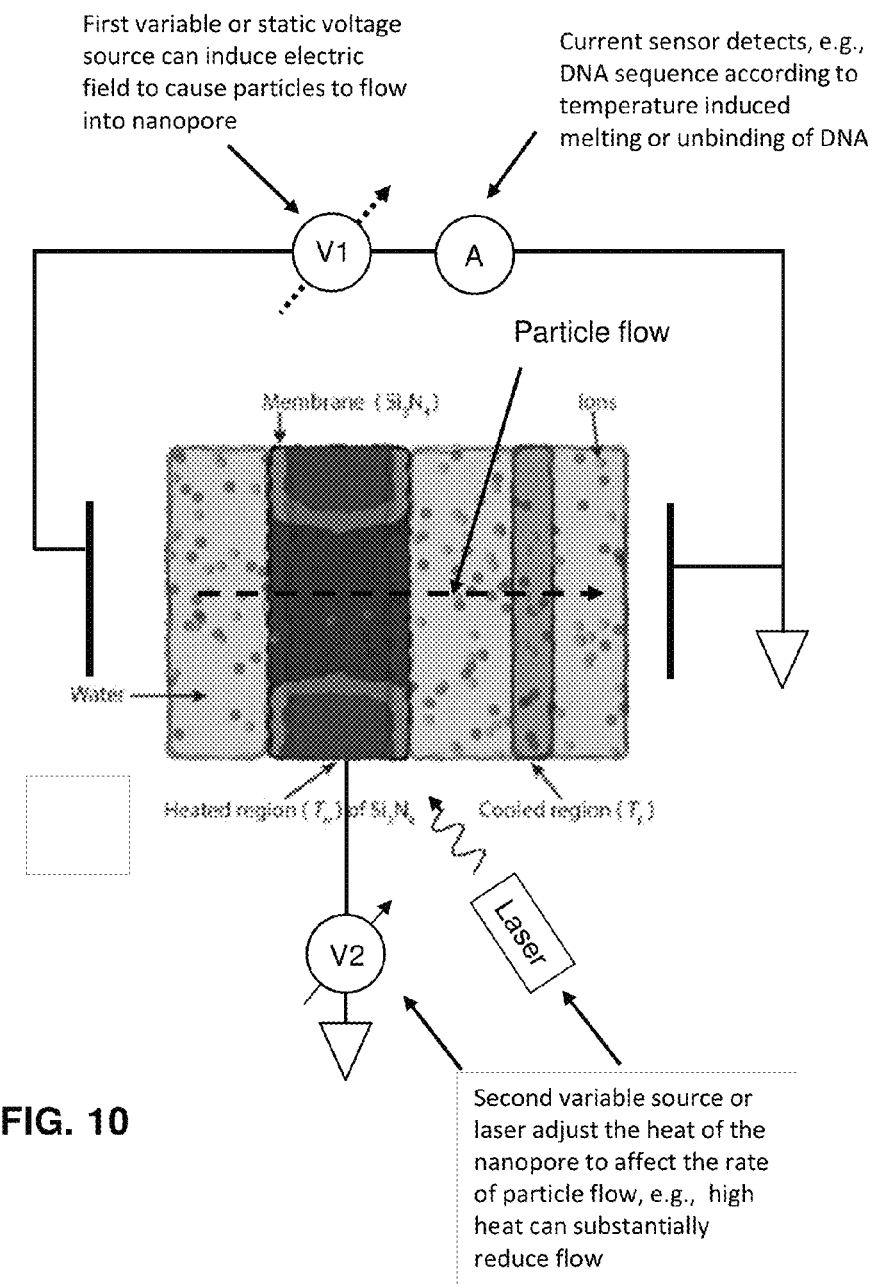
FIG. 10 depicts an illustrative embodiment of the nanopore of FIG. 8 configured to cause ions.
Figure 11:
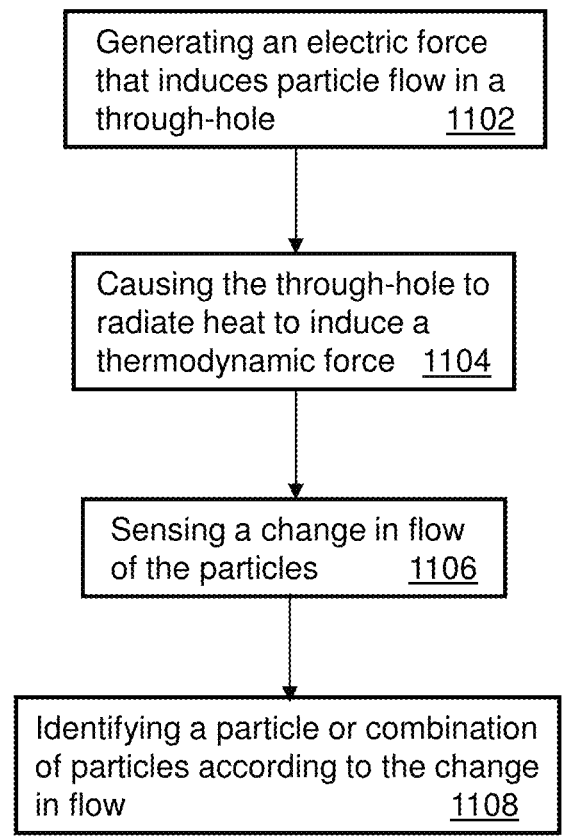
FIG. 11 depicts an illustrative embodiment of a method according to the subject disclosure.

One can use this method to separate different ions and other charged solutes from a solution. Under the influence of an electric field generated by electrodes located at opposite ends of the nanopore (see FIG. 10), charged particles can be forced to move from one side of the membrane to the other through the nanopore (see step 1102, FIG. 11). Alternatively, or in combination with a source supplying the electric field, a pressure source can be used to apply a pressure difference to the solution to induce the flow of particles in the solution through the nanopore. The temperature gradient in the nanopore created by the application of a voltage or laser pulses to the nanopore membrane (see FIG. 10) can impart a thermodynamics force that competes with the electric force (see step 1104, FIG. 11). Since the electric force depends on the charge of the particle and the thermodynamic force does not, the system of FIG. 10 is able to separate particles according to their charge and physical dimensions. In addition to separation and purification, the heated nanopore system permits coupling of the temperature gradient to the flux of solutes through the nanopores, which can be used for chemical computing, nanofluidic electronics, catalysis and energy storage.

Another possible application of the subject disclosure exploits the influence of locally enhanced temperature on properties of the biomolecules, which can be used for their accurate identification or catalysis. For example, by locally enhancing temperature in the vicinity of the nanopore, one can monitor protein unfolding by measuring the current with a current sensor (as shown in FIG. 10) of ions flowing through the nanopore (see step 1106, FIG. 11). A sharp change in the nanopore current can indicate the change in the fold of the protein. An analogous method can be used to detect DNA sequence by measuring temperature-dependent unbinding of DNA probes (see step 1108, FIG. 11). In one embodiment, analytes can be detected by measuring the temperature dependence of their dissociation from the surface of the nanopore.

Several methods can produce desired heating of the nanopore membranes. One can use a membrane containing a conducting electrode to heat it by passing electric current through it (Joule heating—see FIG. 10). A thin membrane will heat and cool very rapidly, which can be used to produce a desired temperature effect. Joule heating produced by the ionic current through the nanopore can additionally enhance the temperature gradient. Another method to heat the membrane is to subject it to short pulses of laser radiation tuned to produce rapid heating of the membrane material (see FIG. 10). Simulations show that the strongest effect is expected when the temperature of the entire membrane is rapidly heated and cooled, when several membranes are positioned in parallel (but only one is heated) to create sharp temperature gradients, and when nanopore membrane is locally heated only in the region surrounding the nanopore. The latter can be achieved by exploiting phase transitions in the membrane material produced by the nanopore manufacturing process, such as electron beam bombardment, which can produce partial crystallization of amorphous membrane (such as alumina) around the nanopore. The local heating effect can be produced by tuning a laser frequency to heat mostly or only the material in the immediate vicinity of the nanopore.

Figure 12:
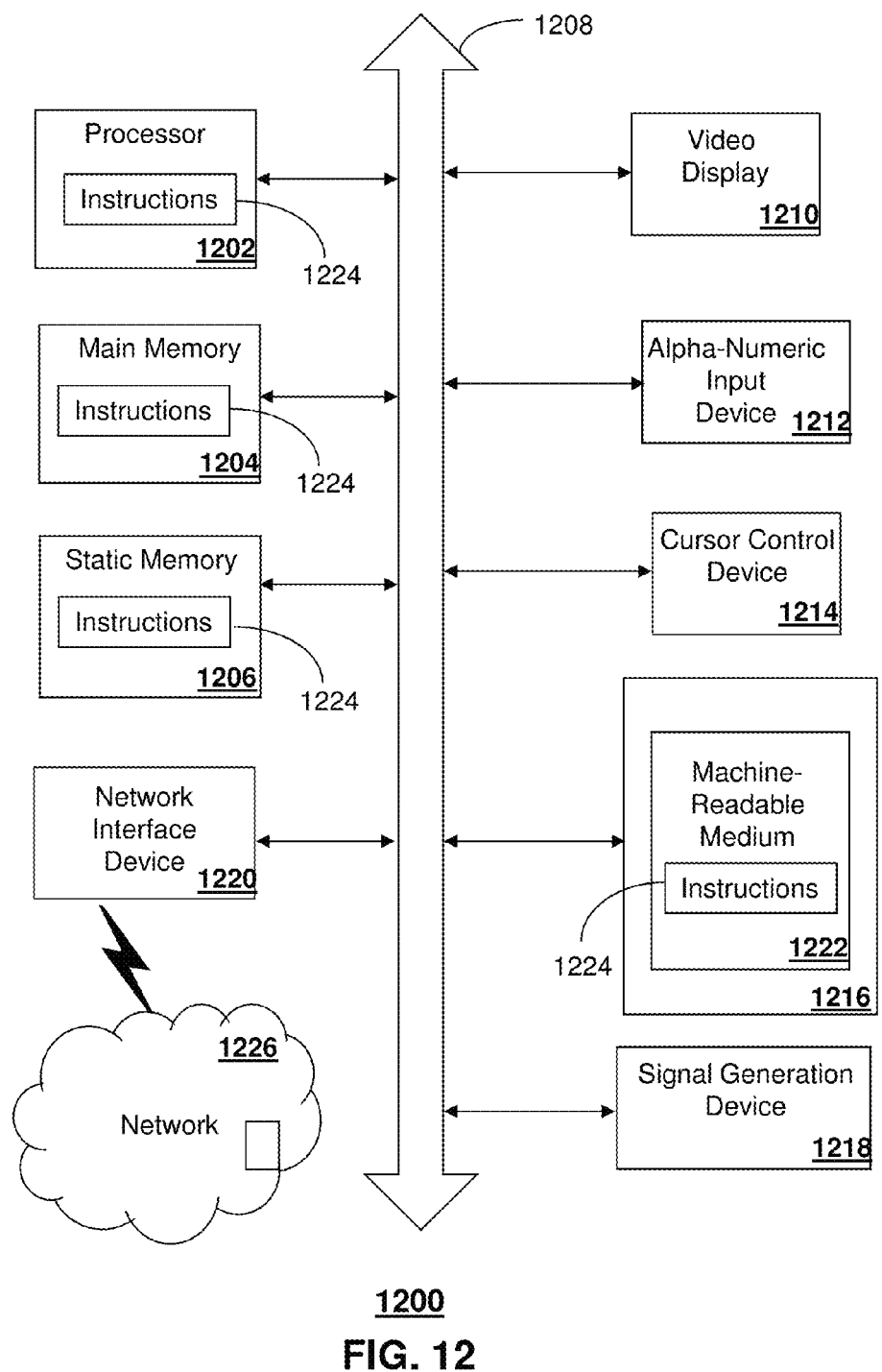
FIG. 12 depicts an illustrative diagrammatic representation of a machine in the form of a computer system within which a set of instructions, when executed, may cause the machine to perform any one or more of the methodologies disclosed herein.

FIG. 12 depicts an exemplary diagrammatic representation of a machine in the form of a computer system 1200 within which a set of instructions, when executed, may cause the machine to perform any one or more of the methods discussed above. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1200 may include a processor 1202 (e.g., a central processing unit (CPU), a graphics processing unit (GPU, or both), a main memory 1204 and a static memory 1206, which communicate with each other via a bus 1208. The computer system 1200 may further include a video display unit 1210 (e.g., a liquid crystal display (LCD), a flat panel, or a solid state display. The computer system 1200 may include an input device 1212 (e.g., a keyboard), a cursor control device 1214 (e.g., a mouse), a disk drive unit 1216, a signal generation device 1218 (e.g., a speaker or remote control) and a network interface device 1220.

The disk drive unit 1216 may include a tangible computer-readable storage medium 1222 on which is stored one or more sets of instructions (e.g., software 1224) embodying any one or more of the methods or functions described herein, including those methods illustrated above. The instructions 1224 may also reside, completely or at least partially, within the main memory 1204, the static memory 1206, and/or within the processor 1202 during execution thereof by the computer system 1200. The main memory 1204 and the processor 1202 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 622 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 1200.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A device, comprising:
   a vessel for carrying a liquid medium having a plurality of particles;
   a substrate having a through-hole;
   a heater element embedded at least in part in the substrate, wherein the heater element is proximal to the through-hole and that facilitates generation of heat in the through-hole, wherein the heater element can be selectively heated by electromagnetic radiation;
   a first conductor located above the through-hole;
   a second conductor located below the through-hole, wherein the first and second conductors are coupled to a first source to cause an electric field between the first and second conductors, and wherein the electric field induces a flow of the plurality of particles through the through-hole; and
   a second source that facilitates generation of the electromagnetic radiation that causes the heater element to be heated, thereby resulting in a temperature gradient in the through-hole to cause an adjustable thermodynamic force that modifies the flow of the plurality of particles through the through-hole.

2. The device of claim 1, further comprising a third conductor coupled to the heater element to facilitate application of an electrical signal on the heater element for selectively adjusting heat generated in the through-hole.

3. The device of claim 1, wherein the second source comprises a laser configured to generate the electromagnetic radiation that is absorbed by the heater element for selectively adjusting heat generated in the through-hole.

4. The device of claim 3, wherein the laser is configured to generate the electromagnetic radiation in pulses to produce rapid heating of the through-hole.

5. The device of claim 1, comprising a sensor for sensing a change in flow of the plurality of particles.

6. The device of claim 5, wherein the change in the flow of the plurality of particles results from one or more particles of the plurality of particles being separated by the thermodynamic force induced by the second source adjusting heat generated in the through-hole.

7. The device of claim 6, wherein the one or more particles separate according to at least one of a charge of each of the one or more particles, a physical dimension of each of the one or more particles, or both.

8. The device of claim 6, wherein the one or more particles separate upon an action of the heat generated in the through-hole.

9. The device of claim 1, wherein the through-hole is a nanopore.

10. The device of claim 9, comprising a sensor for enabling one of chemical computing, nanofluidic electronics, catalysis, or energy storage based on a coupling of the temperature gradient to a flux of solutes through the nanopore.

11. The device of claim 9, wherein the nanopore is asymmetrical.

12. The device of claim 9, wherein the nanopore is symmetrical.

13. The device of claim 1, wherein at least one of the plurality of particles is biomolecule comprising drug molecules, dissociated ions, or both.

14. The device of claim 13, wherein the biomolecule is a protein.

15. The device of claim 13, comprising a sensor for sensing the biomolecule and its epigenetic modifications, wherein the biomolecule is at least one of a deoxyribonucleic acid (DNA) material, a ribonucleic acid (RNA) material, or one or more proteins.

16. A method, comprising:
    generating an electric force that induces a plurality of particles to flow through a through-hole in a substrate; and
    applying heat to the through-hole by generating electromagnetic radiation that heats one or more materials that are embedded at least in part in the substrate and are proximal to the through-hole resulting in a temperature gradient in the through-hole to induce a thermodynamic force for modifying the flow of the plurality of particles through the through-hole.

17. The method of claim 16, wherein the through-hole is a nanopore, wherein at least one of the plurality particles is a biomolecule.

18. The method of claim 16, wherein the electromagnetic radiation is generated by a laser.

19. The method of claim 16, further comprising sensing a change in flow in the plurality of particles.

20. The method of claim 16, wherein the flow in the plurality of particles is caused by an electric force generated from an electric field emanating from an electrical source.

21. The device of claim 1, wherein the heater element comprises at least a portion of the through-hole.

22. The method of claim 16, wherein the one or more materials comprise at least a portion of the through-hole.

23. The method of claim 19, further comprising identifying at least one of the plurality of particles according to the change in flow.

24. The method of claim 19, wherein the change in flow is sensed by measuring a change in ion current flow through the through-hole.

25. The method of claim 22, wherein the at least one of the plurality of particles is a biomolecule comprising at least one of a drug molecule, a dissociated ion, a protein, a deoxyribonucleic acid (DNA), or a ribonucleic acid (RNA).

* * * * *